United States Patent [19]
Roe et al.

[11] Patent Number: 5,667,503
[45] Date of Patent: *Sep. 16, 1997

[54] DIAPER HAVING EXPULSIVE SPACER

[75] Inventors: Donald Carroll Roe, West Chester; Kimberly Ann Dreier, Cincinnati, both of Ohio

[73] Assignee: The Procter & Gamble Company, Cincinnati, Ohio

[*] Notice: The term of this patent shall not extend beyond the expiration date of Pat. No. 5,514,121.

[21] Appl. No.: 441,269

[22] Filed: May 15, 1995

Related U.S. Application Data

[62] Division of Ser. No. 353,578, Dec. 9, 1994, Pat. No. 5,514,121.

[51] Int. Cl.⁶ .................................................. A61F 13/15
[52] U.S. Cl. ............................................... 604/385.1
[58] Field of Search ........................ 604/385.1, 385.2, 604/398

[56] References Cited

U.S. PATENT DOCUMENTS

| | | | |
|---|---|---|---|
| 3,604,423 | 9/1971 | Fraser | 604/385.1 |
| 4,022,212 | 5/1977 | Lovison | 604/385.2 |
| 4,072,150 | 2/1978 | Glassman | 128/284 |
| 4,559,051 | 12/1985 | Hanson | 604/385.1 |
| 4,702,378 | 10/1987 | Finkel et al. | 604/385.1 |
| 4,892,536 | 1/1990 | Desmarais et al. | 604/385.2 |
| 4,964,857 | 10/1990 | Osborn | 604/395 |
| 4,968,312 | 11/1990 | Khan | 604/385.1 |
| 4,990,147 | 2/1991 | Freeland | 604/385.2 |
| 5,037,416 | 8/1991 | Allen et al. | 604/385.1 |
| 5,069,672 | 12/1991 | Wippler et al. | 604/385.1 |
| 5,171,236 | 12/1992 | Dreier et al. | 604/369 |
| 5,269,775 | 12/1993 | Freeland et al. | 604/385.2 |
| 5,306,266 | 4/1994 | Freeland | 604/385.1 |
| 5,330,459 | 7/1994 | Lavon et al. | 604/385.1 |
| 5,344,516 | 9/1994 | Tanji et al. | 604/385.2 |
| 5,360,422 | 11/1994 | Brownlee et al. | 604/385.2 |

FOREIGN PATENT DOCUMENTS

| | | |
|---|---|---|
| A 604 580 | 9/1978 | Switzerland . |
| 2 242 821 A | 10/1991 | United Kingdom . |
| 2 256 803 A | 12/1992 | United Kingdom . |
| WO89/11842 | 12/1989 | WIPO . |

*Primary Examiner*—Michael J. Milano
*Attorney, Agent, or Firm*—Larry L. Huston; E. Kelly Linman; Jacobus C. Rasser

[57] ABSTRACT

A disposable absorbent article such as a diaper. The diaper has a topsheet, backsheet, and an intermediate core. Affixed to the outwardly oriented surface of the topsheet is an expulsive spacer. The spacer receives and collects fecal material from the wearer. The spacer may be removable from the diaper, or may be articulable relative to the diaper. By expelling the spacer from the diaper, fecal material can be easily flushed into the toilet, rather than discarded into a waste receptacle where it presents a sanitation hazard.

3 Claims, 3 Drawing Sheets

DIAPER HAVING EXPULSIVE SPACER

This is a divisional of application Ser. No. 08/353,578, filed on Dec. 9, 1994 now U.S. Pat. No. 5,514,121, May 7, 1996.

FIELD OF THE INVENTION

This invention is related to disposable absorbent articles, particularly to disposable absorbent articles such as diapers which receive fecal material, and more particularly to disposable absorbent articles having spacers which allow for containment and isolation of fecal material.

BACKGROUND OF THE INVENTION

Disposable absorbent articles, such as diapers, are well known in the art. These articles address the consumers' demands for increased convenience. In particular, disposable absorbent articles which minimize cleaning of the wearer after the article is soiled and removed are convenient. A particularly desired feature providing such convenience is to minimize cleaning of fecal material present on the wearer's skin after the soiled disposable absorbent article is removed.

Several attempts have been made in the art to isolate the fecal material from the skin of the wearer. Such attempts frequently relied upon a topsheet which hugged the skin of the wearer, allowing a void space to form between the topsheet and the absorbent core. Illustrative of such attempts in the art are commonly assigned U.S. Pat. No. 4,892,536 issued Jan. 9, 1990 to DesMarais et al.; U.S. Pat. No. 4,990,147 issued Feb. 5, 1991 to Freeland; U.S. Pat. No. 5,037,416 issued Aug. 6, 1991 to Allen et al.; and U.S. Pat. No. 5,269,775 issued Dec. 14, 1993 to Freeland et al., which patents are incorporated herein by reference for the purpose of showing how to create a void space in a disposable absorbent article, such as a diaper.

It became apparent that further advances in the art were necessary. Subsequent advances interposed a spacer between the topsheet and the absorbent core. The spacer created the void space to capture and isolate the fecal material, even if the wearer was sitting. Later advances in the art recognized the desirability of making the spacers flexible and inflatable. Illustrative of such advances in the art are commonly assigned U.S. Pat. No. 5,171,236 issued Dec. 15, 1992 to Dreier et al.; U.S. Pat. No. 5,306,266 issued Apr. 26, 1994 to Freeland; and U.S. Pat. No. 5,330,459 issued Jul. 19, 1994 to LaVon et al., which patents are incorporated herein by reference for the purpose of showing spacers particularly suitable for use in conjunction with the present invention.

While the spacers of the aforementioned diapers have been technically successful, they have met with limited consumer acceptance. Frequently the consumer desires to remove the fecal material from the diaper and into the toilet, so that the fecal material can be flushed away—rather than discarded with the diaper in the trash. Discarding the disposable absorbent article into the trash while it still contains a significant quantity of fecal material raises sanitation concerns and causes malodors to accumulate. Unfortunately, the spacers of the prior art disposable absorbent articles retain the fecal material, still performing the intended function of isolating the fecal material from the wearer.

Accordingly, it is an object of the present invention to provide a disposable absorbent article having a spacer. It is further an object of the present invention to provide a disposable absorbent article having a spacer which does not retain fecal material when the disposable absorbent article is removed from the wearer and discarded. Finally, it is an object of this invention to provide a disposable absorbent article having an expulsive spacer.

SUMMARY OF THE INVENTION

The present invention comprises a disposable absorbent article having a chassis comprising a liquid pervious topsheet, a liquid impervious backsheet, and an absorbent core between the topsheet and the backsheet. The topsheet has both inwardly and outwardly oriented surfaces. Disposed on the outwardly oriented surface of the topsheet is an expulsive spacer. The spacer is movable relative to the chassis, so that fecal material in the spacer may be discarded separately from the chassis. In one embodiment the spacer may be completely detachable from the topsheet. In a second embodiment the spacer may be articulable and expel the fecal material upon articulation from a first wearing position to a second discarding position.

DETAILED DESCRIPTION OF THE INVENTION

As used herein, the term "absorbent article" refers to devices which absorb and contain body exudates and are placed against or in proximity to the body of the wearer to absorb and contain discharges. The term "disposable" describes absorbent articles not intended to be laundered or otherwise restored or reused (i.e., they are intended to be discarded after a single use and preferably recycled, composted, or otherwise disposed of in an environmentally compatible manner). A "unitary" absorbent article refers to an article formed of separate parts united together to form a coordinated entity that does not require separate manipulative parts, like a separate holder and liner. A preferred embodiment of a disposable absorbent article of the present invention is the unitary disposable absorbent article, diaper 20, shown in FIG. 1. As used herein the term "diaper" refers to a disposable absorbent article generally worn by infants and incontinent persons about the lower torso. It should be understood, however, that the present invention is also applicable to other disposable absorbent articles such as incontinence briefs, incontinence undergarments, and diaper holders and liners.

Figure 1:
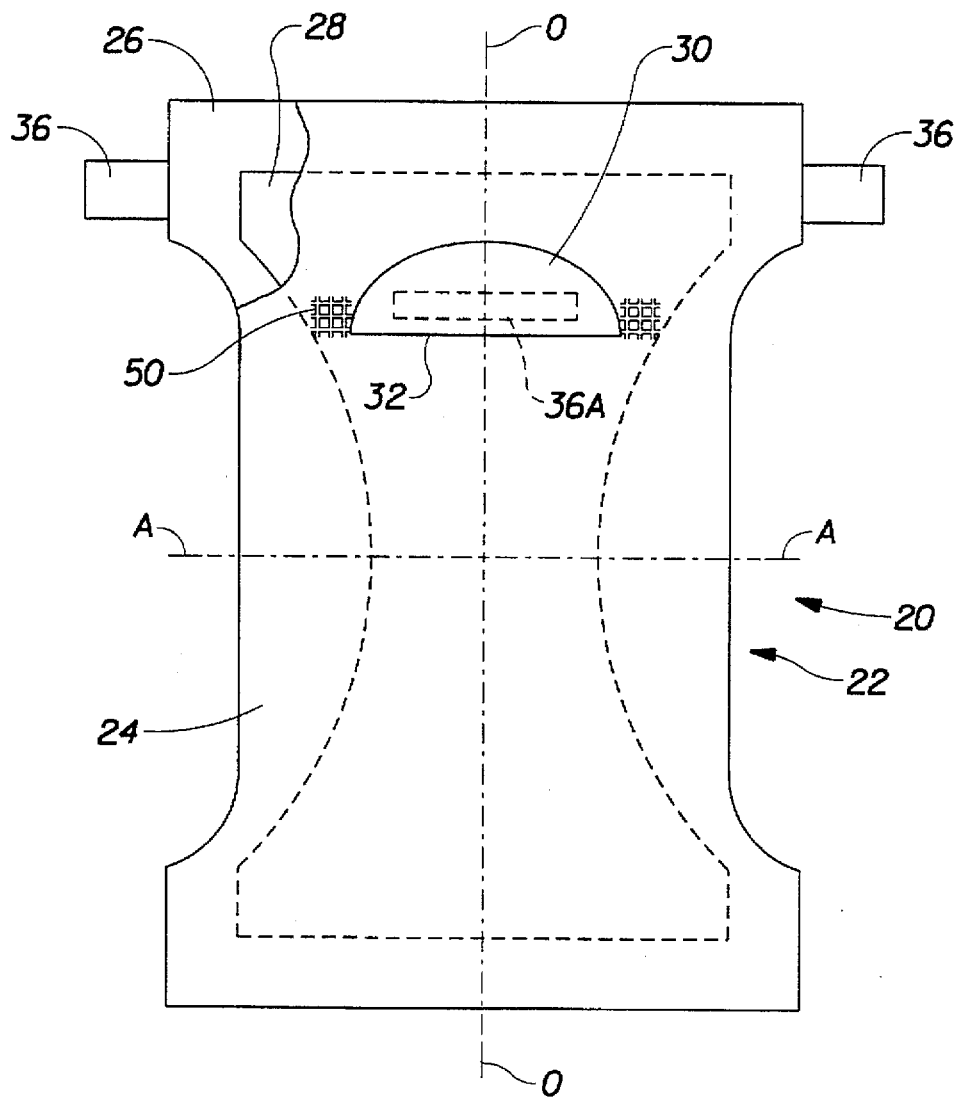
FIG. 1 is a top plan view, shown partially in cutaway, of a diaper according to the present invention having an expulsive spacer releasably affixed to the topsheet.

FIG. 1 is a plan view of diaper 20 of the present invention in its flat, uncontracted state (with elastic induced contraction pulled out, and portions of the structure cut away to more clearly show the construction of the diaper 20). The portion of the diaper 20 which faces or contacts the wearer, i.e., the inner surface, is oriented towards the viewer. The diaper 20 has a longitudinal centerline O—O and a lateral centerline A—A. As used here in the longitudinal centerline O—O or dimension is aligned front to back and bisects the standing wearer into left and right body halves. The lateral centerline A—A or dimension is orthogonal the longitudinal centerline O—O and lies within the plane of the diaper 20. The Z-direction is orthogonal to both the longitudinal and lateral directions and comes out of the plane of the diaper 20.

The diaper 20 has a chassis 22 comprising a liquid pervious topsheet 24, a liquid impervious backsheet 26 at least partially peripherally joined to the topsheet 4, and an absorbent core 28 between the topsheet 24 and the backsheet 26. The topsheet 24 has an inwardly oriented surface which is oriented towards the core 28, and an outwardly oriented surface which is oriented towards and/or contacts the wearer. Attached to the outwardly oriented surface of the topsheet 24 is an expulsive spacer 30. The spacer 30 is movable relative to the chassis 22.

The diaper 20 may also include tape fasteners 36 positioned in the rear waist region for fastening the diaper 20 about the wearer. The diaper 20 can also have an elastic waistband (not shown) and leg cuffs, such as gasket leg cuffs (not shown), and/or barrier leg cuffs 29. Commonly assigned U.S. Pat. No. 3,848,594 issued Nov. 19, 1974 to Buell, Re B1 4,662,875 reissued May 5, 1987 to Hirotsu et al.; are incorporated herein by reference to illustrate tape fasteners 36; U.S. Pat. No. 3,860,003 issued Jan. 14, 1975 to Buell; U.S. Pat. No. 4,081,301 issued Mar. 21, 1978 to Buell; U.S. Pat. No. 4,695,278 issued Sep. 22, 1987 to Lawson; U.S. Pat. No. 4,808,177 issued Feb. 8, 1989 to DesMarais; and U.S. Pat. No. 4,938,755 issued Jul. 3, 1990 to Foreman, are incorporated herein by reference to illustrate gasket cuffs and barrier leg cuffs 29; and U.S. Pat. No. 4,515,595 issued May 17, 1985 to Kiev; and U.S. Pat. No. 4,816,025 issued Mar. 28, 1989 to Foreman, are incorporated herein by reference to illustrate elasticized waist features.

The topsheet 24 and backsheet 26 of the diaper 20 have longitudinal and lateral dimensions generally larger than those of the absorbent core 28, so that the topsheet 24 and backsheet 26 may extend beyond the core 28 to thereby form the periphery of the diaper 20. The embodiment described herein is suitable for a wearer weighing about 7.3 to about 12.7 kilograms (16 to 28 pounds). It will he understood that if the diaper 20 is intended for use with larger or smaller wearers, including adults, the diaper 20, including the expulsive spacer 30, will have to be scaled accordingly.

Examining the components of the diaper 20 in more detail, the topsheet 24 and backsheet 26 are generally coextensive and at least partially peripherally joined. As used herein, the term "joined" refers to the condition where a first member or component is affixed or connected to a second member or component, either directly or indirectly where the first member or component is directly affixed to the second member or component, or connected to an intermediate member or component which in turn is affixed or connected to the second member or component. Components which are "joined" are intended to remain affixed or connected throughout the intended life of the diaper 20 and not to be separated unless and until the diaper 20 is discarded and as may be necessary for environmentally compatible disposal. Components which are "joined" cannot be separated without tearing or gross deformation of one or both components.

The topsheet 24 refers to any liquid pervious facing of the diaper 20 which contacts the skin of the wearer and prevents substantial contact of the absorbent core 28 with the skin of the wearer. The topsheet 24 is compliant, tactilely pleasant, and non-irritating to the skin.

A suitable topsheet 24 may be manufactured from porous foams, apertured plastic films, natural fibers, synthetic fibers, or a combination thereof. A particularly preferred topsheet 24 comprises polypropylene fibers and may be manufactured as a nonwoven web of spunbonded, carded, wet laid, melt blown, hydroentangled fibers. A particularly preferred topsheet 24 is carded and thermally bonded to have a basis weight of 14 to 25 grams per square meter. A suitable topsheet 24 is marketed by Veratec Inc., Division of International Paper Company, of Walpole, Mass. under the designation The backsheet 26 is impervious to fluids such as urine and prevents fluids absorbed and contained by the core 28 from wetting the undergarments. As used herein, the "backsheet" refers to any barrier disposed outwardly of the core 28 as the diaper 20 is worn and which contains absorbed liquid within the diaper 20. The backsheet 26 is preferably manufactured from a thin plastic film, although other flexible, liquid impervious materials may be used. As used herein, the term "flexible" refers to materials which are compliant and will readily conform to the general shape of the human body.

The backsheet 26 may be a polyolefinic tint, such as polyethylene, having a thickness of about 0.01 to 0.05 millimeters. A suitable backsheet 26 can be made from a blend of 45 to 90 percent LLDP and about 10 to 55 percent polypropylene. Exemplary backsheet rims are sold by Tredegar Industries of Terre Haute, Ind. under the designation RR8220 and RR5475.

The topsheet 24 and backsheet 26 may be joined by any means well known in the art, such as adhesive bonding or heat sealing. A particularly preferred method of joining the topsheet 24 and backsheet 26 is with hot melt adhesives such as are manufactured by Century Adhesives, Inc. of Columbus, Ohio and marketed as Century 5227, or BL1258 adhesive sold by the H. B. Fuller Company of St. Paul, Minn., or H2031 available from the Findley Adhesives Company of Elmgrove, Wis.

As used herein, the term "core" refers to any component of the diaper 20 intermediate the topsheet 24 and backsheet 26 and used for absorbing and retaining body exudates. The core 28 may be encased by one or more layers of tissue (not shown).

The absorbent core 28 may be made from a variety of materials such as comminuted wood pulp and may further contain particulate or fibrous absorbent gelling materials as are commonly known in the an. The absorbent core 28 may be made in accordance with the teachings of commonly assigned U.S. Pat. No. 4,610,678 issued Sep. 9, 1986 to Weisman et al.; U.S. Pat. No. 5,137,537 issued Aug. 11, 1992 to Herron et al.; and U.S. Pat. No. 5,147,345 issued Sep. 15, 1992 to Young et al., which patents are incorporated herein by reference. Absorbent gelling materials, if desired, may be made in accordance with commonly assigned U.S. Patent No. Re. 32,649, reissued Apr. 19, 1988 to Brandt et al.

The spacer 30 of the present invention may either be releasably affixed to the outwardly oriented face of the topsheet 24, or may be permanently joined thereto, depending upon the particular embodiment. The spacer 30 collects and receives fecal material, thereby preventing it from excessively spreading and smearing against the skin of the wearer. The spacer 30 may be oriented longitudinally concave towards the front waist margin, longitudinally concave towards the rear waist margin, may be a closed figure, or may simply present a straight barrier.

The spacer 30 according to the present invention is "expulsive." By expulsive it is meant the spacer 30 moves from a first position to a second position and thereby expels or releases at least a portion of the fecal material contained therein from the diaper 20. The movement may or may not detach the expulsive spacer 30 from the diaper 20. The spacer 30 may have a size and geometry according to the previously incorporated U.S. Pat. Nos. 5,171,236; 5,306,266; and 5,330,459.

Figure 2:
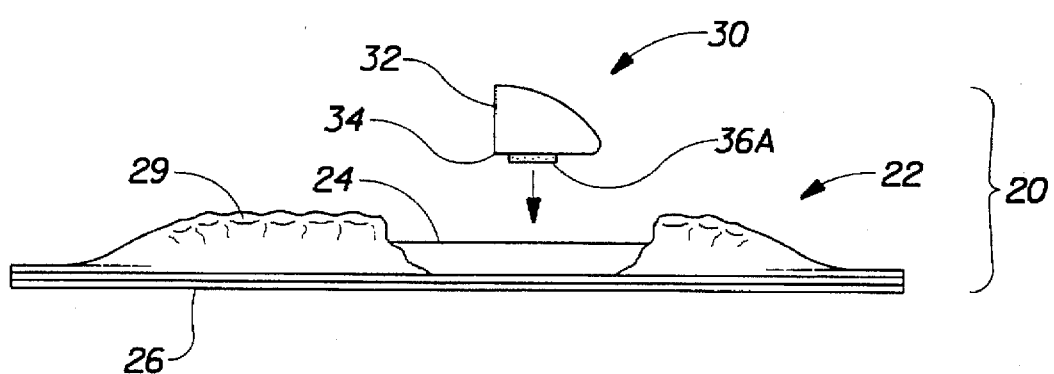
FIG. 2 is an exploded side elevational view of the diaper of FIG. 1.

Referring to FIG. 2, the spacer 30 may be releasably affixed to the diaper 20 and removed, in combination with any fecal material contained therein when it is desired to discard the diaper 20. Optionally, the spacer 30 may be made of a material that is flushable so that it may be conveniently disposed of. A flushable spacer 30 may be made of tissue or other cellulosic material.

By "releasably affixed" it is meant that in contrast to being joined, the spacer 30 is, by manufacture, removable from the topsheet 24 without tearing or gross deformation of either component, and is conveniently detached from the topsheet 24 by the user. Components which are "joined" together as described above are not considered releasably affixed within the context of the present invention.

The spacer 30 may be releasably affixed to the outer surface of the topsheet 24 by pressure sensitive adhesive disposed on fastening tabs 36A. Suitable adhesives include A-305-IV from Century Adhesives Corporation of Columbus, Ohio and Instant Lock 34-2823 from National Starch and Chemical Company, of Bridgewater, N.J. If desired, landing zones may be joined to the outwardly oriented surface of the topsheet 24 to make the spacer 30 easier to release therefrom. A particularly preferred landing zone may be made from the fastening surface material disclosed in the aforementioned U.S. Patent No. B 1 4,662,875.

Alternatively, the spacer 30 may be releasably affixed to the topsheet 24 by hook and loop fastening systems on the fastening tabs 36A, as are well known in the art. Suitable hook and loop fastening systems may be made according to commonly assigned U.S. Pat. No. 5,318,741 issued Jun. 7, 1994 to Thomas; U.S. Pat. No. 5,116,563 issued May 26, 1992 to Thomas et al.; or U.S. Pat. No. 5,058,247 issued Oct. 22, 1991 to Thomas et al., which patents are incorporated herein by reference, or may be purchased as commercially available materials from Velcro U.S.A. of Manchester, N.H. or GuilFord Fabric of Greensboro, N.C.

If the hook and loop fastening system is selected for Fastening tabs 36A, preferably the receiving material, rather than the hook type fasteners, comprises the landing zone for attachment of the spacer 30 to the topsheet 24. Of course, it will be recognized that if hooks of the proper size and shape are selected, a dedicated landing zone may not be necessary, and the spacer 30 may be joined directly to the outwardly oriented surface of the topsheet 24. However, as noted above, it is preferable that the diaper 20 not comprise hooks extending outwardly from the surface of the topsheet 24, otherwise abrasion against the skin of the wearer may occur.

If a releasably affixed spacer 30 is selected, as illustrated in FIGS. 1 and 2, the spacer 30 may be made of a nonwoven material, have an opening facing forward, and generally spanning the lateral distance between the barrier leg cuffs 29, if used with the diaper 20. If barrier leg cuffs 29 are not used in conjunction with the diaper 20 of the present invention, the spacer 30 may generally span the lateral width of the core 28.

Figure 3:
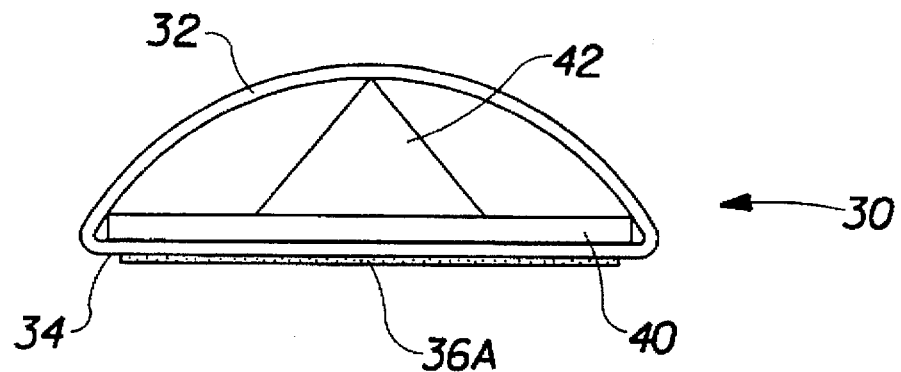
FIG. 3 is a frontal view of the spacer of the diaper of FIGS. 1 and 2.

Referring to FIG. 3, the spacer 30 may be made of a nonwoven material such as a web of staple length polypropylene fibers, commonly manufactured by companies such as Veratec Inc., Division of International Paper Company of Walpole, Mass. under the designation P-8. The distal edge 32 defining the opening of the spacer 30 may be elasticized to all the distal edge 32 of the spacer 30 away from the plane of the topsheet 24, and/or to pull the distal edge 32 of the spacer 30 towards the end of the diaper 20 and away from the lateral centerline A—A. If desired, the spacer 30 may have a generally rectangular base 40 joined to the nonwoven material. The base may be made of foam and provides rigidity to the spacer 30, improving the releasable attachment to the topsheet 24, whether or not a landing zone is present.

Preferably the spacer 30 is made of a material which is flushable. Flushable materials are well known in the art. However, a particularly suitable flushable material may be made of tissue paper, as is well known in the art, and can be made according to commonly assigned U.S. Pat. No. 4,191,609 issued Mar. 4, 1980 to Trokhan, or U.S. Pat. No. 4,637,858 issued Jan. 20, 1987 to Trokhan, which patents are incorporated herein by reference. A suitable tissue paper may have a basis weight of 25 pounds per 3,000 square feet, and may be coated with a low viscosity hot melt adhesive. The hot melt adhesive, such as is available from the H.B. Fuller Company of Wauwatosa, Wis. and sold under product number HL-1412-X has been found suitable and may be applied at a basis weight of 10 to 30 pounds per 3,000 square feet to yield a laminate having a total basis weight of 35 to 55 pounds pet 3,000 square feet.

If desired, the spacer 30 may further comprise an internal flame 42 to insure the spacer 30 remains open while in use. As used herein, "an internal frame" refers to any member which opens the distal edge 32 of the spacer 30 so that the spacer 30 can suitably receive fecal material. A suitable internal frame 42 may also be made of foam. A particularly suitable internal frame 42 is triangularly shaped. The triangularly shaped internal frame 42 may have a flat end proximate the base 40 of the spacer 30 and extend upwardly to a tip distal from the base 40. If desired, the base 40 of the spacer 30 and the internal frame 42 may be made of a unitary piece of foam. Suitable foam for use with the base 40 and/or internal frame 42 of the spacer 30 is made by The Voltek Division of Sekisui of America Corporation of Lawrence, Mass. under the designation Volara 2A PE white foam.

The topsheet 24 according to the present invention may comprise indicia 50, visible on or through the topsheet 24. The indicia 50 assist the caretaker in properly aligning and positioning the spacer 30. The indicia 50 may be printed on, or applied to the outwardly oriented surface of the topsheet 24, using any of the means well known in the art. The indicia 50 should not cause epidermal irritation. Providing the topsheet 24 is not too opaque or translucent, the indicia 50 may be applied to the surface of the topsheet 24 facing the absorbent core 28.

Figure 4:
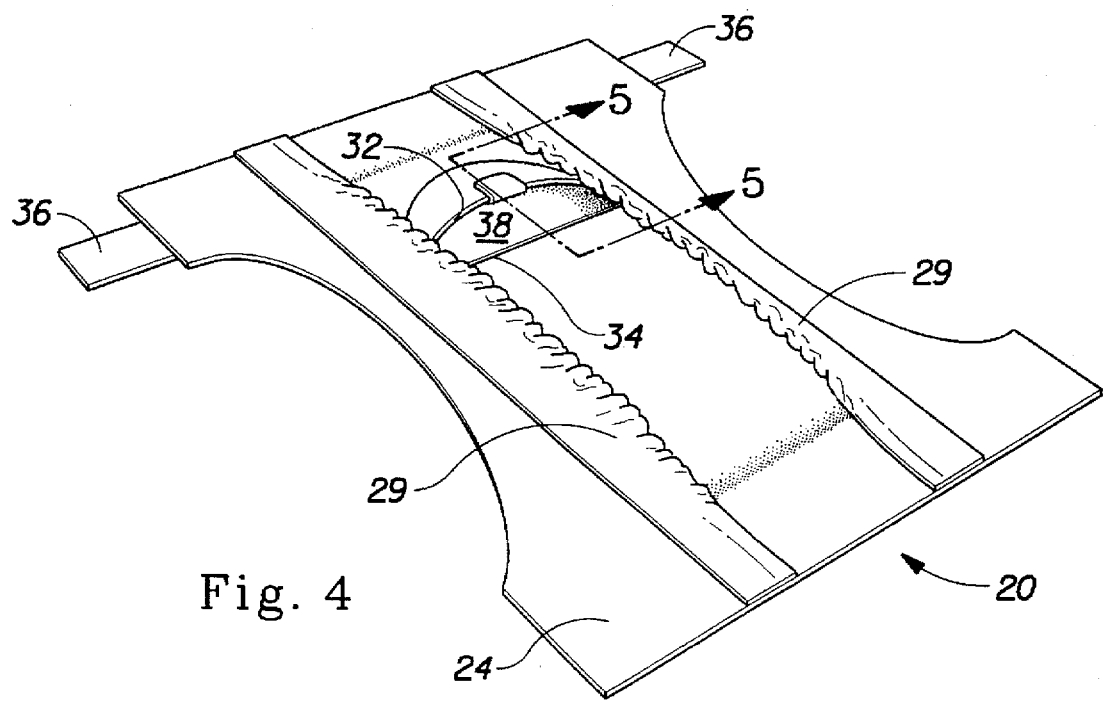
FIG. 4 is a perspective view of a diaper according to a second embodiment of the present invention having an articulable spacer joined to the topsheet.

Referring to FIG. 4, if it is desired the expulsive spacer 30 not be releasably affixed to and detachable from the diaper 20, the expulsive spacer 30 may be joined to and articulable relative to the diaper chassis 22. In such an embodiment, the spacer 30 may be generally U-shaped having the ends joined to the barrier leg cuffs 29. Such a spacer 30 may be made of a nonwoven material having elastic at the distal edge 32, as noted above.

Figure 5:
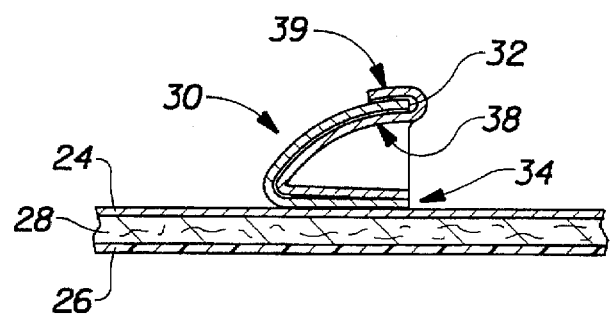
FIG. 5 is an instantaneous vertical sectional view of the liner of FIG. 4 taken along line 5—5, showing the liner in the first position and showing the liner and spacer separated for clarity.

Such a spacer 30 may further comprise an articulable liner 38. The articulable liner 38 of the spacer 30 is disposed in a first wearing position when the diaper 20 is first placed on the wearer. In the wearing position, the liner 38 is nested inside the spacer 30, and is generally contiguous and conformable to the overall shape of the spacer 30 as illustrated in FIG. 5.

Figure 6:
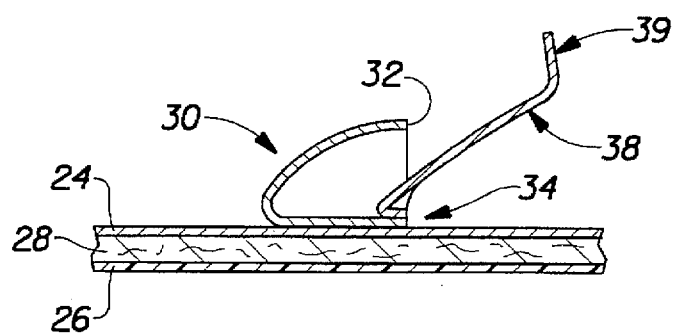
FIG. 6 is an instantaneous vertical sectional view of the liner of FIG. 5 in section, showing the liner articulated to a second position.

When the diaper 20 is to be discarded, and the fecal material expelled from the spacer 30, the spacer 30, or the liner 38, is articulated from the first wearing position to a second discarding position as shown in FIG. 6. The proximal edge 34 of the articulable spacer 30 or articulable liner 38 may be joined to the topsheet 24, and the liner 38 or spacer 30 articulated thereabout in order to expel the fecal material. The direction of the articulation from the first position to the second position is towards the lateral centerline A—A of the diaper 20. If desired, the distal edge 32 of the liner 38 may also be elasticized in order to keep the liner in place while the diaper 20 is worn.

The distal edge 32 of the liner 38 may further comprise a string or a tab 39 juxtaposed with and joined to the distal edge 32 of the liner 38. The string on tab 39 may be tucked under the liner 38, or between the liner 38 and the balance of the spacer 30 when worn, and pulled by the user to articulate the liner 38 from the first position to the second position.

Figure 7:
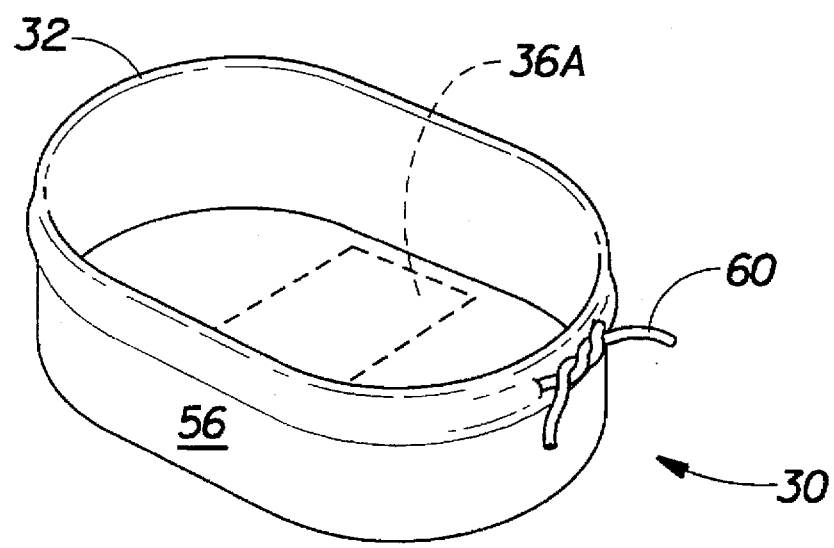
FIG. 7 is a perspective view of a releasably affixable spacer for use with the diaper of FIG. 1, wherein the spacer forms a closed figure.

Referring to FIG. 7, if desired, in an alternative first embodiment the releasably affixed spacer 30 may comprise a closed figure. Such a spacer 30 has sidewalls 56 upstanding from the plane of the topsheet 24. The sidewalls 56 may be made of foam, as disclosed above. The foam may be lined with a nonwoven material for comfort. Such a spacer 30 may be generally oval shaped and have dimensions of about 9×6 centimeters. This spacer 30 has the particular advantage that while the foam provides conformability and comfort to the wearer, the fecal material is well contained therein and easily discarded by the caretaker while minimizing soiling of his or her hands. If desired, the sidewalls 56 of this spacer 30 may be releasably affixed to upstanding barrier leg cuffs 29.

Yet another advantage of the closed figure spacer 30 is that the distal edge 32 may be elasticized or even have a drawstring at the distal edge 32 of the spacer 30. In this arrangement, the drawstring may be pulled upon removal of the spacer 30 from the balance of the diaper 20 to reduce the size of the opening and enclose the fecal material therein.

One benefit of the present invention is that the diaper 20 and releasably affixed spacer 30 may be separately packaged and sold. For example, if desired, a package may contain a commercially suitable number of diapers 20 and a lesser number of such spacers 30. Alternatively, the releasably affixed spacer 30 may be packaged and sold (individually or with a plurality of other spacers 30) independently of the diaper 20. This arrangement allows the consumer the flexibility to use the diapers 20 when only urine loading is expected. However, when fecal material loadings are expected, the consumer can then add the spacer 30 to the diaper 20 to accommodate this expected loading.

It will be apparent there are many other variations of the present invention which are feasible. For example, combinations of the foregoing spacers 30 are feasible, all of which variations are within the scope of the appended claims.

What is claimed is:

1. A diaper having a longitudinal centerline and a lateral centerline orthogonal thereto, said lateral centerline dividing said diaper into front and rear portions, said diaper comprising:
   a chassis comprising:
      a liquid impervious backsheet;
      a liquid pervious topsheet having an inwardly oriented surface and an outwardly oriented surface;
      an absorbent core intermediate said topsheet and said backsheet, said core facing said inwardly oriented surface of said topsheet; and
      an arcuately shaped expulsive spacer adhesively releasably affixed to said topsheet and being disposed on said outwardly oriented surface of said topsheet and having a concave side and a convex side, said expulsive spacer being oriented such that said concave side faces towards said front portion of said diaper, and receivably collecting fecal material deposited on said outwardly oriented surface of said topsheet, whereby said spacer can expel at least a portion of the fecal material contained therein.

2. A diaper comprising:
   a chassis comprising:
      a liquid impervious backsheet;
      a liquid pervious topsheet having an inwardly oriented surface and an outwardly oriented surface;
      an absorbent core intermediate said topsheet and said backsheet, said core facing said inwardly oriented surface of said topsheet;
      two longitudinally oriented barrier leg cuffs, said barrier leg cuffs being spaced apart in the lateral direction; and
      an expulsive spacer releasably affixed to said outwardly oriented surface of said topsheet, said expulsive spacer having an opening extending entirely throughout the lateral spacing between said barrier leg cuffs to suitably receive fecal material, said opening remaining open while said spacer is in use.

3. A diaper comprising:
   a chassis comprising:
      a liquid impervious backsheet;
      a liquid pervious topsheet having an inwardly oriented surface and an outwardly oriented surface;
      an absorbent core intermediate said topsheet and said backsheet, said core facing said inwardly oriented surface of said topsheet;
      an expulsive spacer joined to said outwardly oriented surface of said topsheet, said spacer having an opening to receive fecal material which is deposited on said outwardly oriented surface of said topsheet; and
      a flushable liner comprising tissue paper nested inside said expulsive spacer, whereby said liner may be removed from said diaper, so that fecal material received therein may be discarded separately from said chassis.

* * * * *

UNITED STATES PATENT AND TRADEMARK OFFICE
CERTIFICATE OF CORRECTION

PATENT NO. : 5,667,503
DATED : September 16, 1997
INVENTOR(S) : DONALD CARROLL ROE et al.

It is certified that error appears in the above-indentified patent and that said Letters Patent is hereby corrected as shown below:

Column 1, line 38, "an" should read -- art --.
Column 1, line 44, "an" should read -- art --.
Column 2, line 63, "he" should read -- be --.
Column 3, line 17, "4," should read -- 24, --.
Column 3, line 47, "he" should read -- be --.
Column 4, line 16, after "designation" insert -- P-8. --.
Column 4, line 27, "tint," should read -- film, --.
Column 4, line 31, "rims" should read -- films --.
Column 4, line 52, "an." should read -- art. --.
Column 5, line 53, "Fastening" should read -- fastening --.
Column 6, line 34, "pet" should read -- per --.
Column 6, line 36, "flame" should read -- frame --.
Column 6, line 42, "fiat" should read -- flat --.

Signed and Sealed this

Ninth Day of November, 1999

Attest:

Q. TODD DICKINSON

*Attesting Officer*     *Acting Commissioner of Patents and Trademarks*